(12) United States Patent
Kibayashi

(10) Patent No.: US 10,398,289 B2
(45) Date of Patent: Sep. 3, 2019

(54) IMAGE PICKUP UNIT AND ENDOSCOPE

(71) Applicant: OLYMPUS CORPORATION, Tokyo (JP)

(72) Inventor: Takehide Kibayashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/241,793

(22) Filed: Aug. 19, 2016

(65) Prior Publication Data
US 2016/0353977 A1 Dec. 8, 2016

Related U.S. Application Data
(63) Continuation of application No. PCT/JP2015/053646, filed on Feb. 10, 2015.

(30) Foreign Application Priority Data
Feb. 25, 2014 (JP) .................................. 2014-034509

(51) Int. Cl.
A61B 1/00 (2006.01)
A61B 1/05 (2006.01)
(Continued)

(52) U.S. Cl.
CPC ........ *A61B 1/00096* (2013.01); *A61B 1/0011* (2013.01); *A61B 1/00183* (2013.01);
(Continued)

(58) Field of Classification Search
CPC ............ A61B 1/00163; A61B 1/00188; A61B 1/0019; A61B 1/00064; A61B 1/00071;
(Continued)

(56) References Cited

U.S. PATENT DOCUMENTS

2009/0067067 A1 3/2009 Yamaya
2009/0303619 A1 12/2009 Iwasaki et al.
(Continued)

FOREIGN PATENT DOCUMENTS

EP 2 130 482 A1 12/2009
EP 2 581 028 A1 4/2013
(Continued)

OTHER PUBLICATIONS

Japanese Office Action dated Jan. 12, 2016 issued in Japanese Patent Application No. 2015-545577.
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An image pickup unit includes a fixed frame configured to hold an objective lens, a moving frame movable in a first direction along a photographing optical axis and a second direction, and provided with a moving lens, an urging member configured to urge the moving frame in the second direction, an actuator including a contact member provided to be separable from the moving frame and advanced and retracted by pushing and pulling of a driving wire, the actuator moving the moving frame in the first direction when the contact member moves in the first direction; and a guide member through which the contact member is inserted to be linearly guided and a cover member configuring the actuator, a distal end portion of the cover member being connected to a proximal end portion of the guide member, and the cover member covering the driving wire.

6 Claims, 12 Drawing Sheets

(51) Int. Cl.
*H04N 5/225* (2006.01)
*G02B 23/24* (2006.01)
*H04N 5/232* (2006.01)

(52) U.S. Cl.
CPC .......... *A61B 1/00188* (2013.01); *A61B 1/05* (2013.01); *G02B 23/243* (2013.01); *G02B 23/2476* (2013.01); *H04N 5/2254* (2013.01); *H04N 5/2256* (2013.01); *H04N 5/23293* (2013.01); *H04N 2005/2255* (2013.01)

(58) Field of Classification Search
CPC ...... A61B 1/005; A61B 1/0051; G02B 23/24; H04N 5/2254; H04N 5/2256; H04N 5/23293; H04N 2005/2255
USPC ................................ 600/109, 160, 167, 168
See application file for complete search history.

(56) References Cited

U.S. PATENT DOCUMENTS

| | | | |
|---|---|---|---|
| 2012/0162402 A1* | 6/2012 | Amano | A61B 1/00096 348/65 |
| 2012/0220828 A1 | 8/2012 | Iwasaki | |

FOREIGN PATENT DOCUMENTS

| | | | |
|---|---|---|---|
| JP | 57130601 U | * | 8/1982 |
| JP | H02-103009 A | | 4/1990 |
| JP | 2002-191553 A | | 7/2002 |
| JP | 2003-290134 A | | 10/2003 |
| JP | 2009-061185 A | | 3/2009 |
| JP | 2009-291364 A | | 12/2009 |
| JP | 2009-294540 A | | 12/2009 |
| JP | 2009-300761 A | | 12/2009 |
| JP | 2010-046424 A | | 3/2010 |
| JP | 2011-010671 A1 | | 1/2011 |
| JP | 5155494 B | | 3/2013 |
| WO | 00/15143 A1 | | 3/2000 |
| WO | 2008/127886 A1 | | 10/2008 |
| WO | 2012/063816 A1 | | 5/2012 |

OTHER PUBLICATIONS

International Search Report dated Apr. 21, 2015 issued in International Patent Application No. PCT/JP2015/053646.
Extended Supplementary European Search Report dated Sep. 28, 2017 in European Patent Application No. 15 75 4835.5.

* cited by examiner

IMAGE PICKUP UNIT AND ENDOSCOPE

CROSS REFERENCE TO RELATED APPLICATION

This application is a continuation application of PCT/JP2015/053646 filed on Feb. 10, 2015 and claims benefit of Japanese Application No. 2014-034509 filed in Japan on Feb. 25, 2014, the entire contents of which are incorporated herein by this reference.

BACKGROUND OF THE INVENTION

1. Field of the Invention

The present invention relates to an image pickup unit that varies optical characteristics of an objective optical system used in an endoscope and the like and an endoscope provided with the image pickup unit.

2. Description of the Related Art

As is well known, endoscopes are widely used for observation, treatment, and the like of an inside of a body (an inside of a body cavity) of an organism or inspection, repairing, and the like of a plant facility for industrial use. In recent years, there is an endoscope in which an image pickup unit that can change a focal length is used for focus adjustment of a photographed image or a zooming function for performing magnification adjustment such as wide/tele. Note that a technique of the image pickup unit that can change the focal length in this way is used not only in the endoscope but also in various photographing devices.

For example, Japanese Patent Application Laid-Open Publication No. 2003-290134 discloses an image pickup unit provided in an endoscope apparatus. The conventional image pickup unit is configured to be capable of advancing and retracting a moving lens, which is a variable focus lens, along an optical axis to an always-focused focal position when an operation wire disposed in an insertion section is pushed and pulled from an operation section by a focus switching lever provided in the operation section.

SUMMARY OF THE INVENTION

An image pickup unit according to an aspect of the present invention includes: a fixed frame configured to hold an objective lens; a moving frame disposed in the fixed frame to be movable in a first direction along a photographing optical axis and a second direction on an opposite side of the first direction, and provided with a moving lens; an urging member disposed in the fixed frame and configured to urge the moving frame in the second direction; an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and a tubular guide member fixed to the fixed frame and including a guide hole through which the contact member is inserted to be guided to advance and retract, wherein a cover member configuring the actuator, a distal end portion of the cover member being connected to a proximal end portion of the guide member, and the cover member covering the driving wire, wherein the contact member has an outer diameter smaller than an inner diameter of the guide hole over an entire length in an advancing and retracting direction and is insertable into and retractable from the guide member, the cover member includes a peeling section in which a plurality of slits are formed in a position extrapolated and firmly attached to the proximal end portion of the guide member, and the driving wire includes an exposed section exposed in a state in which the cover member is peeled in the peeling section, the exposed section enabling the contact member fixed to the driving wire to be removed.

An image pickup unit according to another aspect of the present invention includes: a fixed frame configured to hold an objective lens; a moving frame disposed in the fixed frame to be movable in a first direction along a photographing optical axis and a second direction on an opposite side of the first direction, and provided with a moving lens; an urging member disposed in the fixed frame and configured to urge the moving frame in the second direction; an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and a tubular guide member fixed to the fixed frame and including a guide hole through which the contact member is inserted to be guided to advance and retract, wherein a cover member configuring the actuator, a distal end portion of the cover member being connected to a proximal end portion of the guide member, and the cover member covering the driving wire, wherein the contact member has an outer diameter smaller than an inner diameter of the guide hole over an entire length in an advancing and retracting direction and is insertable into and retractable from the guide member, the cover member includes a cuttable section formed to be capable of being cut in a position where only the driving wire is covered near the proximal end portion of the guide member, and the driving wire includes an exposed section exposed in a state in which the cover member is cut in the cuttable section, the exposed section enabling the contact member fixed to the driving wire to be removed.

An endoscope according to an aspect of the present invention includes an image pickup unit: a fixed frame configured to hold an objective lens; a moving frame disposed in the fixed frame to be movable in a first direction along a photographing optical axis and a second direction on an opposite side of the first direction, and provided with a moving lens; an urging member disposed in the fixed frame and configured to urge the moving frame in the second direction; an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and a tubular guide member fixed to the fixed frame and including a guide hole through which the contact member is inserted to be guided to advance and retract, wherein a cover member configuring the actuator, a distal end portion of the cover member being connected to a proximal end portion of the guide member, and the cover member covering the driving wire, wherein the contact member has an outer diameter smaller than an inner diameter of the guide hole over an entire length in an advancing and retracting direction and is insertable into and retractable from the guide member, the cover member includes a peeling section in which a plurality of slits are formed in a position extrapolated and firmly attached to the proximal end portion of the guide member, and the driving wire includes an exposed section exposed in a state in which the cover member is peeled in the peeling section, the exposed section enabling the contact member fixed to the driving wire to be removed. The image pickup unit is disposed at a distal end portion of an insertion section.

An endoscope according to another aspect of the present invention includes an image pickup unit: a fixed frame configured to hold an objective lens; a moving frame disposed in the fixed frame to be movable in a first direction along a photographing optical axis and a second direction on an opposite side of the first direction, and provided with a moving lens; an urging member disposed in the fixed frame and configured to urge the moving frame in the second direction; an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and a tubular guide member fixed to the fixed frame and including a guide hole through which the contact member is inserted to be guided to advance and retract, wherein a cover member configuring the actuator, a distal end portion of the cover member being connected to a proximal end portion of the guide member, and the cover member covering the driving wire, wherein the contact member has an outer diameter smaller than an inner diameter of the guide hole over an entire length in an advancing and retracting direction and is insertable into and retractable from the guide member, the cover member includes a cuttable section formed to be capable of being cut in a position where only the driving wire is covered near the proximal end portion of the guide member, and the driving wire includes an exposed section exposed in a state in which the cover member is cut in the cuttable section, the exposed section enabling the contact member fixed to the driving wire to be removed. The image pickup unit is disposed at a distal end portion of an insertion section.

DETAILED DESCRIPTION OF THE PREFERRED EMBODIMENT(S)

The present invention is explained below with reference to the drawings.

In the following explanation, it should be noted that drawings based on an embodiment explained below are schematic and relations between thicknesses and widths of respective portions, ratios of the thicknesses of the respective portions, and the like are different from real ones. Portions having different relations and ratios of dimensions among the portions are sometimes included among the drawings.

First, an embodiment of an endoscope including an image pickup unit according to an aspect of the present invention is explained below with reference to the drawings.

Figure 1:
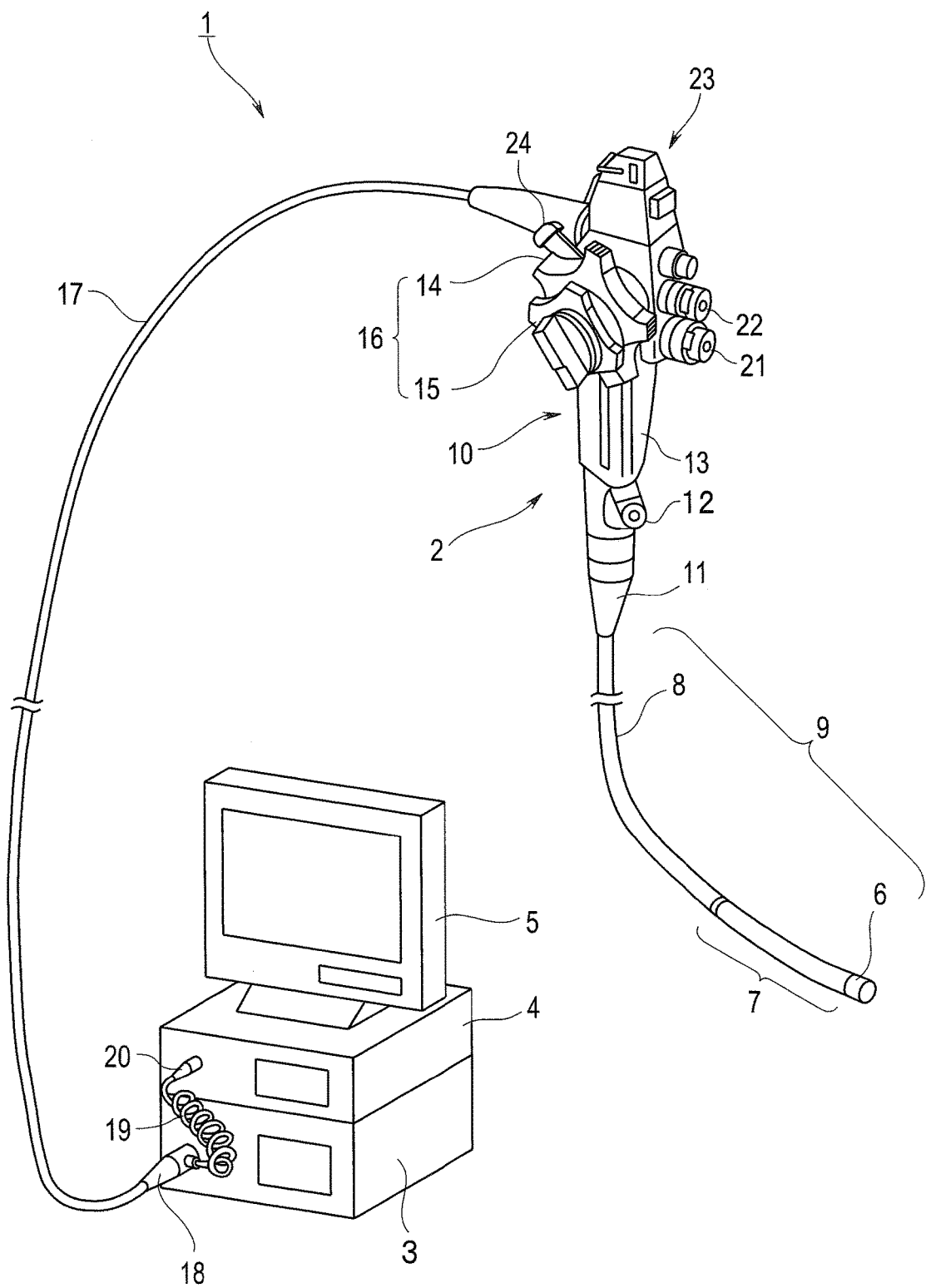
FIG. 1 is a plan view showing an entire configuration of an endoscope.
Figure 2:
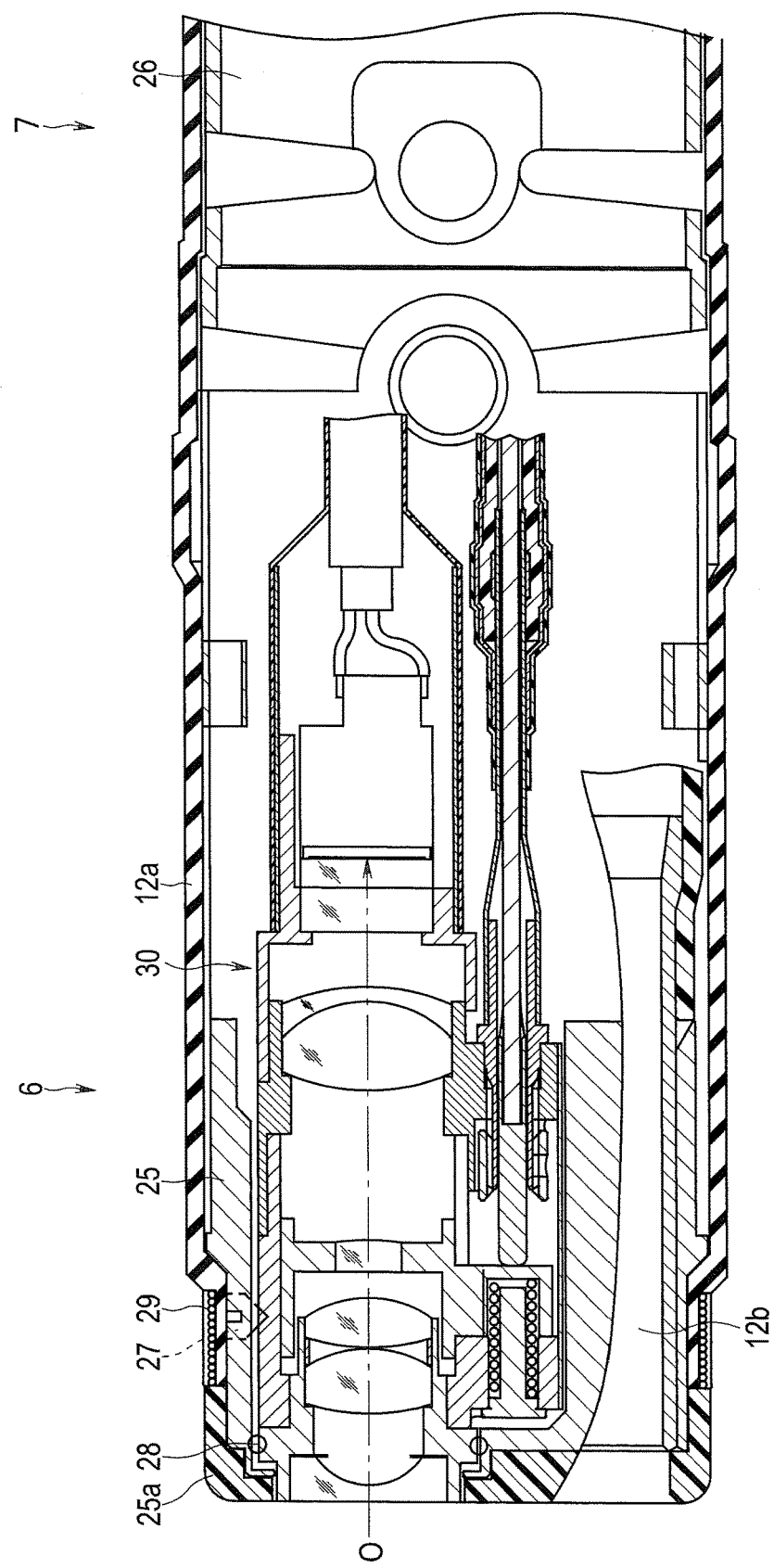
FIG. 2 is a sectional view showing an internal configuration of a distal end portion and a bending section.
Figure 3:
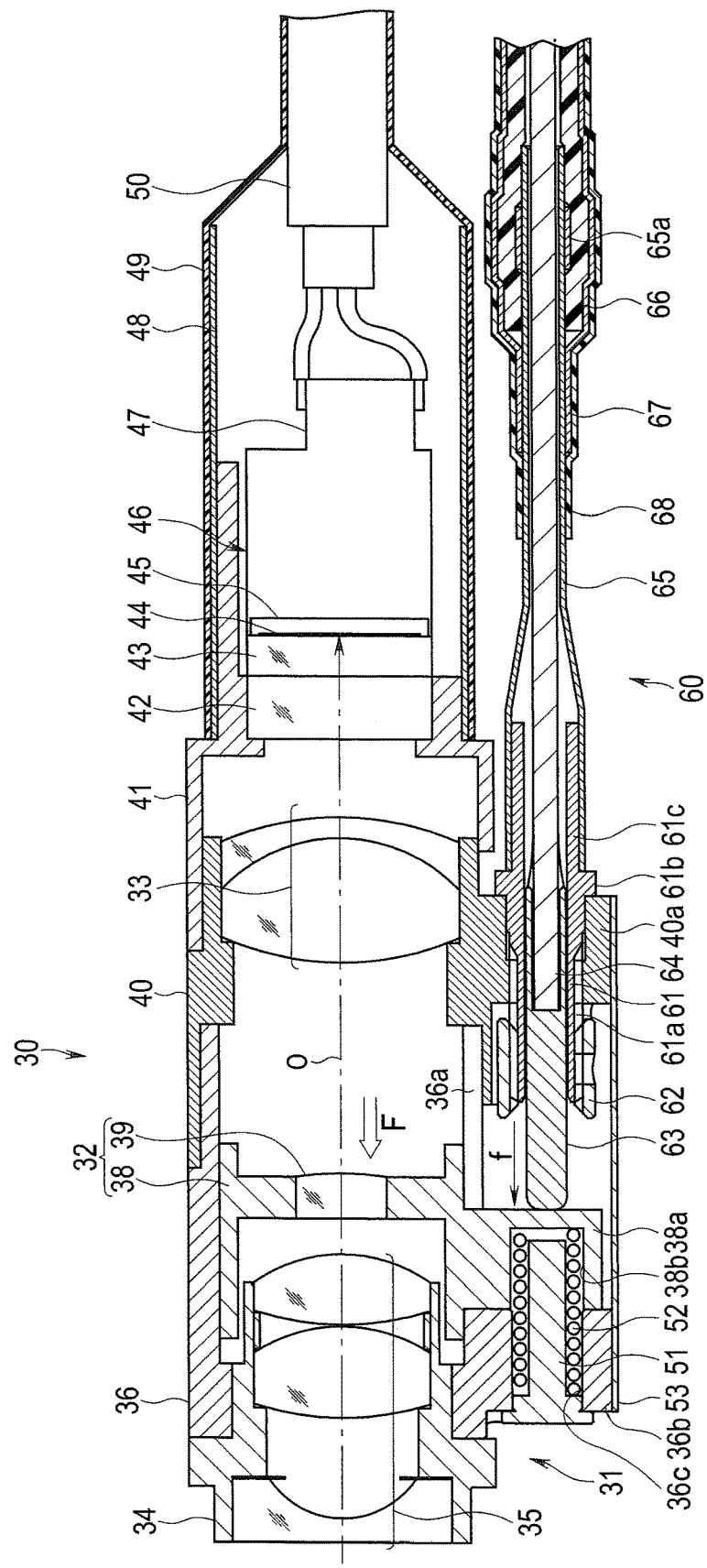
FIG. 3 is a sectional view showing a configuration of an image pickup unit in a state in which a moving lens unit has moved forward.
Figure 4:
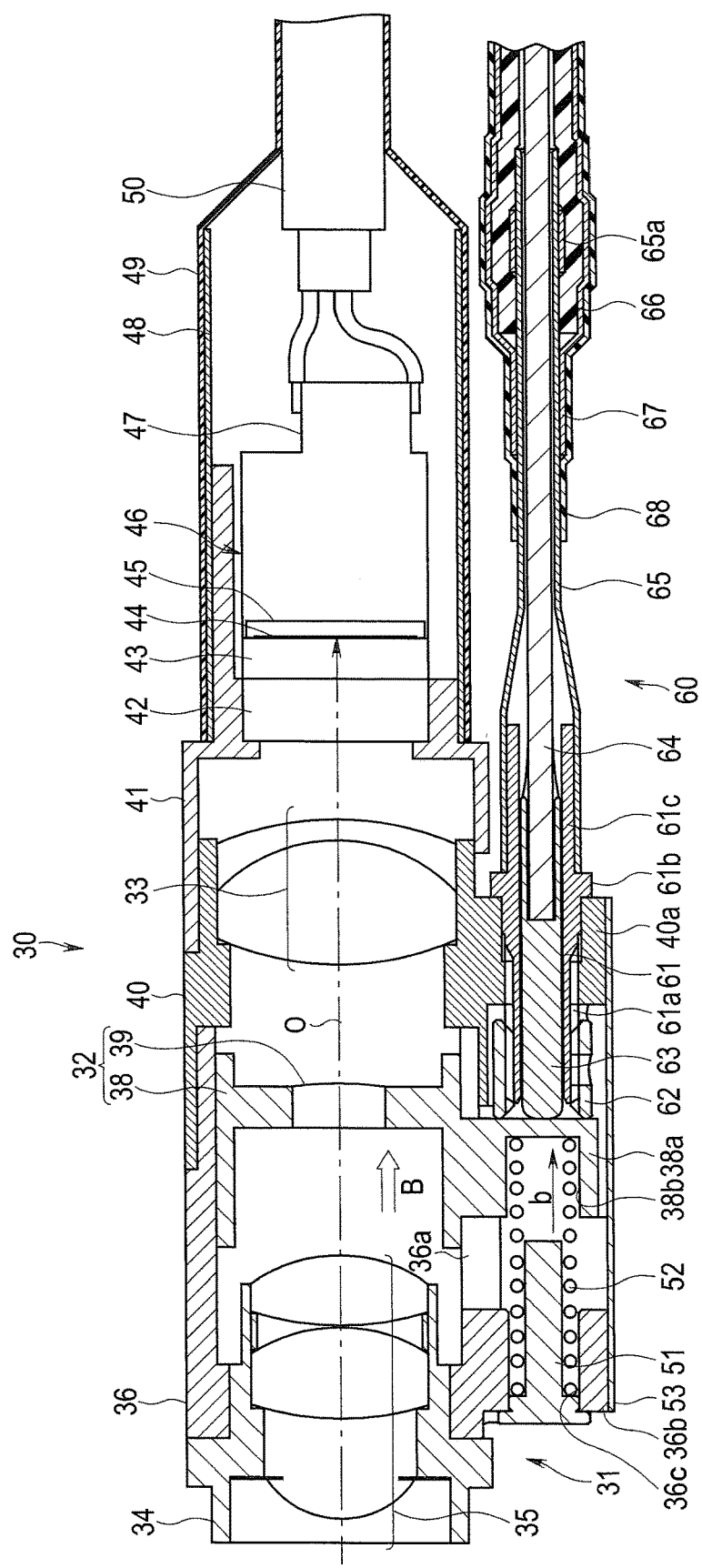
FIG. 4 is a sectional view showing a configuration of the image pickup unit in a state in which the moving lens unit has moved backward.
Figure 5:
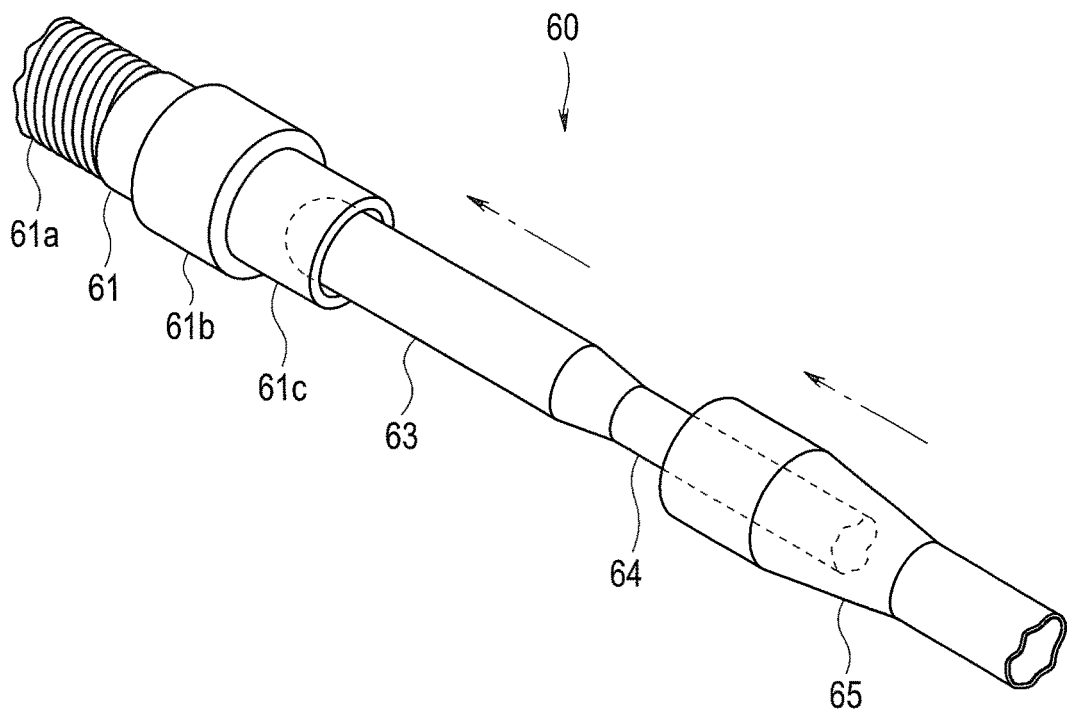
FIG. 5 is an exploded perspective view showing a state in which an actuator is attached to a guide tube.
Figure 6:
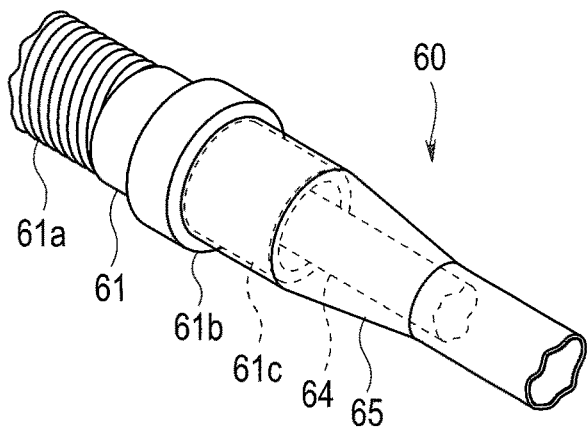
FIG. 6 is a perspective view showing a state in which the actuator has been attached to the guide tube.
Figure 7:
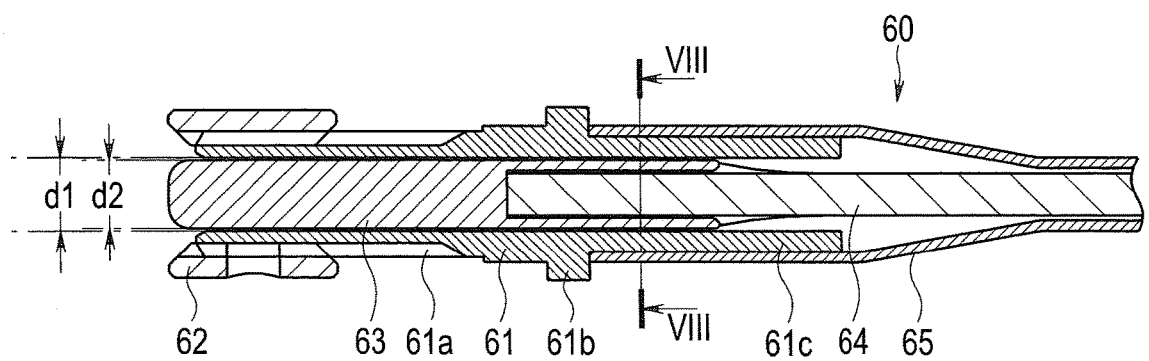
FIG. 7 is a sectional view showing the state in which the actuator has been attached to the guide tube.
Figure 8:
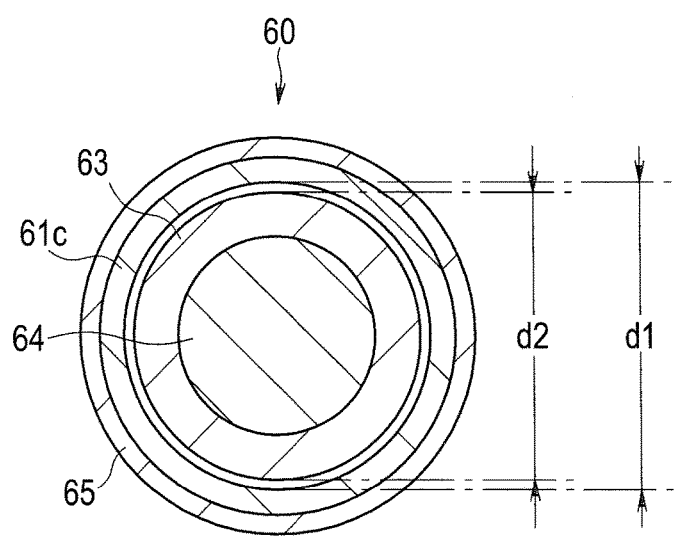
FIG. 8 is a sectional view taken along line VIII-VIII in FIG. 7.
Figure 9:
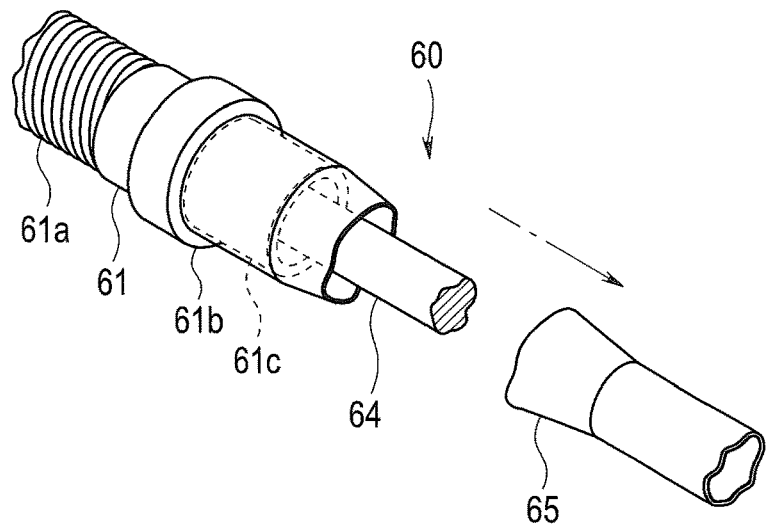
FIG. 9 is a perspective view showing a state in which a cover tube of the actuator is cut.
Figure 10:
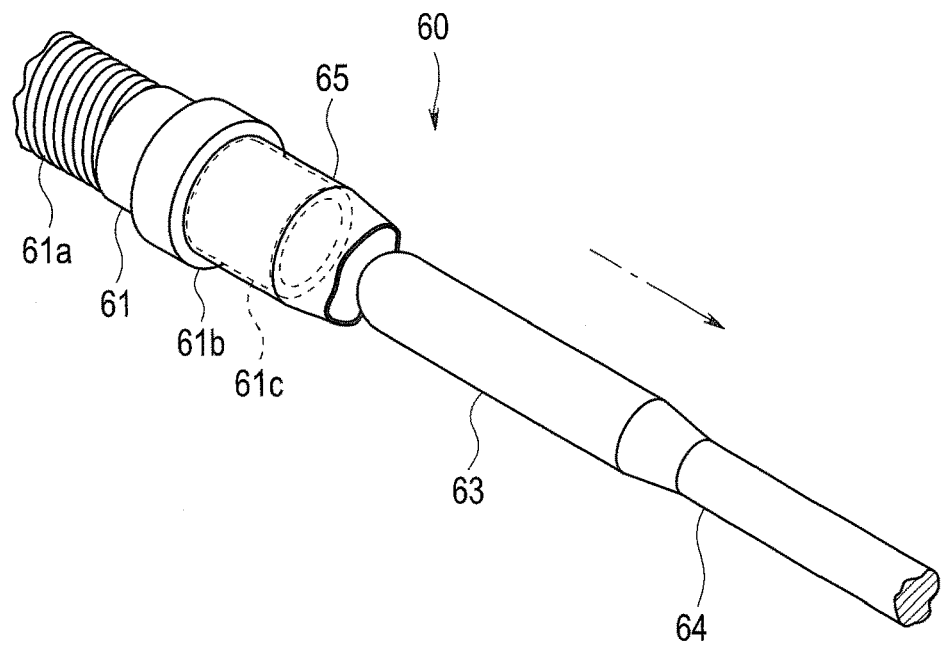
FIG. 10 is a perspective view showing a state in which a rod of the actuator and a driving wire are pulled out from the guide tube.
Figure 11:
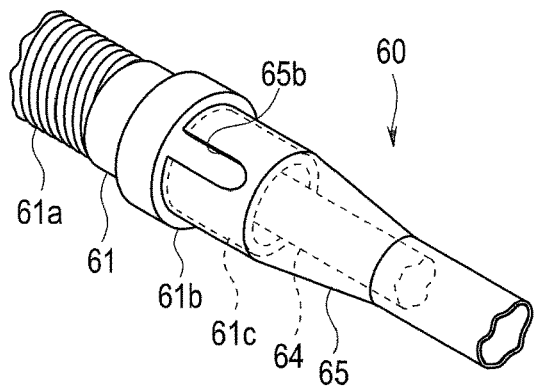
FIG. 11 relates to a first modification and is a perspective view showing a state in which the actuator has been attached to the guide tube.
Figure 12:
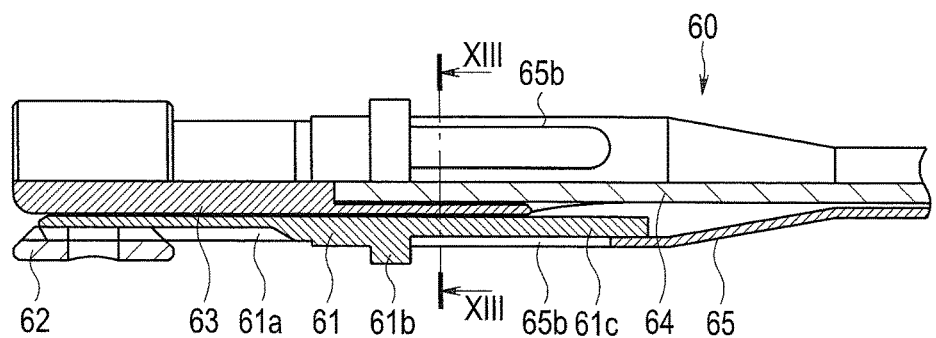
FIG. 12 relates to the first modification and is a partial sectional view and showing the state in which the actuator has been attached to the guide tube.
Figure 13:
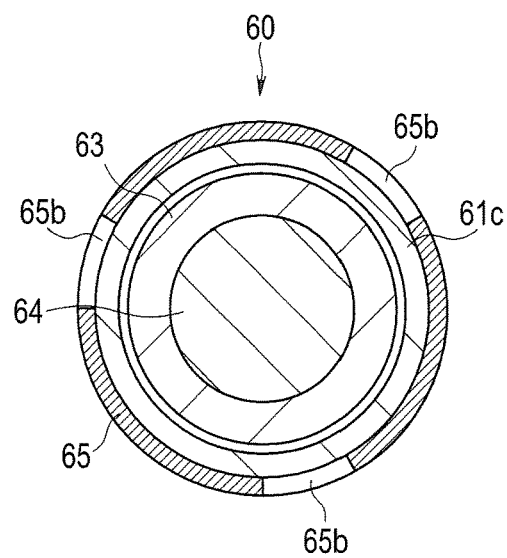
FIG. 13 relates to the first modification and is a sectional view taken along line XIII-XIII in FIG. 12.
Figure 14:
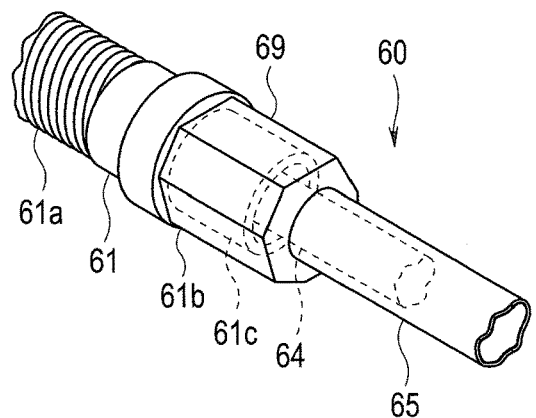
FIG. 14 relates to a second modification and is a perspective view showing a state in which the actuator has been attached to the guide tube.
Figure 15:
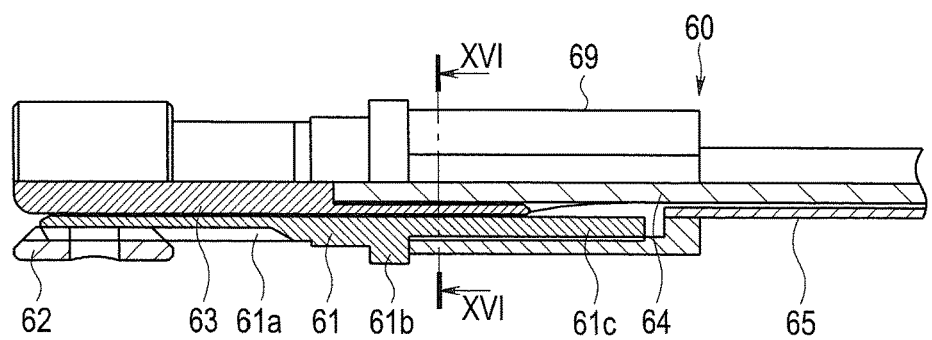
FIG. 15 relates to the second modification and is a partial sectional view showing the state in which the actuator has been attached to the guide tube.
Figure 16:
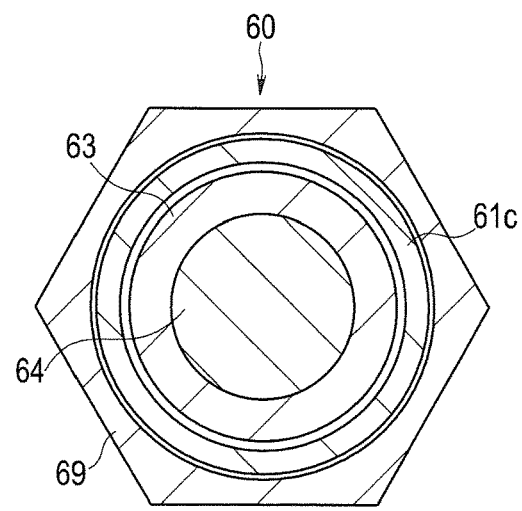
FIG. 16 relates to the second modification and is a sectional view taken along line XVI-XVI in FIG. 15.

FIG. 1 is a plan view showing an entire configuration of an endoscope. FIG. 2 is a sectional view showing an internal configuration of a distal end portion and a bending section. FIG. 3 is a sectional view showing a configuration of the image pickup unit in a state in which a moving lens unit has moved forward. FIG. 4 is a sectional view showing a configuration of the image pickup unit in a state in which the moving lens unit has moved backward. FIG. 5 is an exploded perspective view showing a state in which an actuator is attached to a guide tube. FIG. 6 is a perspective view showing a state in which the actuator has been attached to the guide tube. FIG. 7 is a sectional view showing the state in which the actuator has been attached to the guide tube. FIG. 8 is a sectional view taken along line VIII-VIII in FIG. 7. FIG. 9 is a perspective view showing a state in which a cover tube of the actuator is cut. FIG. 10 is a perspective view showing a state in which a rod of the actuator and a driving wire are pulled out from the guide tube. FIG. 11 relates to a first modification and is a perspective view showing a state in which the actuator has been attached to the guide tube. FIG. 12 relates to the first modification and is a partial sectional view and showing the state in which the actuator has been attached to the guide tube. FIG. 13 relates to the first modification and is a sectional view taken along line XIII-XIII in FIG. 12. FIG. 14 relates to a second modification and is a perspective view showing a state in which the actuator has been attached to the guide tube. FIG. 15 relates to the second modification and is a partial sectional view showing the state in which the actuator has been attached to the guide tube. FIG. 16 relates to the second modification and is a sectional view taken along line XVI-XVI in FIG. 15.

As shown in FIG. 1, an electronic endoscope system (hereinafter simply referred to as endoscope system) 1 in the present embodiment is configured by electrically connecting an electronic endoscope apparatus (hereinafter simply referred to as endoscope) 2, a light source apparatus 3, a video processor 4, and a color monitor 5.

The endoscope 2 includes an insertion section 9 and an operation section 10 from which the insertion section 9 is extended. A universal cord 17 extending from the operation section 10 is connected to the light source apparatus 3 via a scope connector 18.

A coil-like scope cable 19 is extended from the scope connector 18. An electric connector section 20 is provided at the other end portion of the scope cable 19. The electric connector section 20 is connected to the video processor 4.

The insertion section 9 is configured by consecutively connecting a distal end portion 6, a bending section 7, and a flexible tube section 8 in order from a distal end. On a distal end face of the distal end portion 6, a distal end opening section, an observation window, a plurality of illumination windows, an observation window cleaning port, and an observation object cleaning port, which are well known, are disposed (all of which are not shown in the figure).

On a back side of the observation window, an image pickup unit explained below is disposed in the distal end portion 6. On a back side of the plurality of illumination windows, a not-shown light guide bundle, which is inserted through and disposed on an inside of the universal cord 17 from the distal end portion 6, for transmitting illumination light from the light source apparatus 3 is provided.

The observation window cleaning port and the observation object cleaning port configure opening sections of not-shown two cleaning tubes inserted through the inside of the universal cord 17 from the distal end portion 6. The cleaning tubes are connected to, on the light source apparatus 3 side, a cleaning tank, in which not-shown cleaning water is stored, and a compressor.

In the operation section 10, a bend preventing portion 11 from which the insertion section 9 extends, a forceps port 12 disposed on a side portion on a lower side, an operation section main body 13 configuring a grip section of a halfway portion, a bending operation section 16 configured from two bending operation knobs 14 and 15 provided on an upper side, an air/water feeding control section 21, a suction control section 22, a switch section 23 configured from a plurality of switches to mainly operate an image pickup function, and an operation lever 24 for operating a moving lens provided in the image pickup unit explained below to advance and retract and operating, for example, a focusing function of focus adjustment or a zooming function for performing magnification adjustment such as wide/tele are provided.

Note that the forceps port 12 of the operation section 10 configures an opening section of a not-shown treatment instrument channel inserted through and disposed mainly in the insertion section 9 to the distal end opening section of the distal end portion 6.

The configuration of the distal end portion 6 of the endoscope 2 is mainly explained below with reference to FIG. 2.

As shown in FIG. 2, an image pickup unit 30 is disposed on an inside of the distal end portion 6. The image pickup unit 30 is fit and disposed in a rigid distal-end hard member 25 and fixed to the distal-end hard member 25 by a set screw 27 from a side direction.

An O-ring 28 for water tightness is disposed in an outer circumferential portion on a distal end side of the image pickup unit 30. A distal end cover 25a configuring the distal end face of the distal end portion 6 is bonded and fixed to cover a distal end of the distal-end hard member 25.

Note that the distal end opening section, which is a hole portion formed in the distal end cover 25a, configures the opening section of a treatment instrument channel 12b in the distal end portion 6 as explained above.

A distal-end-insertion-section rubber member 12a that integrally covers an outer circumference of the distal-end hard member 25 and a bending piece 26 in the bending section 7 is provided to form external shapes of the distal end portion 6 and the bending section 7.

A distal-end outer circumferential portion of the distal-end-insertion-section rubber member 12a is fixed to the distal-end hard member 25 by a bobbin bonding section 29.

Note that the members such as the cleaning tube and the light guide bundle for illumination disposed in the distal end portion 6 are components well known in the past. Therefore, explanation of the members is omitted.

A configuration of the image pickup unit 30 shown in FIG. 3 and FIG. 4 is explained in detail below.

The image pickup unit 30 in the present embodiment is configured such that a lens on an inside advances and retracts for a focusing function or a zooming function for changing a focal length and varying optical characteristics.

The image pickup unit 30 shown in FIG. 3 includes a front-group lens unit 31 and a moving lens unit 32. The image pickup unit 30 includes a holding frame 36, which is a fixed frame fit on a proximal end side of the front-group lens unit 31 to slide and hold the moving lens unit 32, a rear-group lens frame 40, which is a fixed frame fit in the holding frame 36, and a solid-state-image-pickup-device-unit holding frame 41, which is a fixed frame fit in the rear-group lens frame.

The front-group lens unit 31 includes a front group lens 35 configured from an objective lens and a front-group lens frame 34, which is a fixed frame that holds the front group lens 35.

The moving lens unit 32 includes a moving lens 39 and a moving lens frame 38, which is a moving frame that holds the moving lens 39. The moving lens unit 32 is disposed to be capable of advancing and retracting, on a rear side of the front-group lens unit 31, in a front-back direction (a front side F shown in FIG. 3 and a rear side B shown in FIG. 4) serving as a first direction and a second direction on an opposite side of the first direction along a photographing optical axis O direction in the holding frame 36.

In a moving lens frame 38 of the moving lens unit 32, a protrusion section 38a is formed to extend in an outer diameter direction. Note that, in the holding frame 36, a slit 36a for allowing the protrusion section 38a of the moving lens frame 38 to escape in the outer diameter direction is formed such that the moving lens unit 32 can slide (advance and retract).

A hole section 38b is formed on a front side of the protrusion section 38a of the moving lens frame 38. A compression spring 52 functioning as an urging member is disposed in the hole section 38b. The moving lens unit 32 always receives an urging force of the compression spring 52 on a rear side (in a "b" direction shown in FIG. 4).

The compression spring 52 is disposed in a through-hole 36c formed in the front-back direction of a projecting section 36b extending in the outer diameter direction of the holding frame 36. The compression spring 52 is disposed to be extrapolated to a shaft member 51 provided in a through-hole 36c formed in the projecting section 36b of the holding frame 36.

Note that a proximal end face of the projecting section 36b of the holding frame 36 comes into contact with a distal end face of the protrusion section 38a of the moving lens frame 38 to restrict a forward moving position of the moving lens frame 38.

An outward flange is formed at one end of the shaft member 51. The shaft member 51 is inserted into the through-hole 36c of the projecting section 36b from the front. The outward flange is firmly attached to the projecting section 36b by an adhesive. The shaft member 51 has length extended further backward than a proximal end face of the projecting section 36b and holds the compression spring 52 not to deviate from the front-back direction.

When the moving lens frame 38 moves forward, a proximal end portion of the shaft member 51 further projecting than the proximal end face of the projecting section 36b is housed in the hole section 38b of the protrusion section 38a.

The rear-group lens frame 40 holds a rear group lens 33 configured from a plurality of objective lenses. A holding rod 40a extending in a convex shape in the outer diameter direction is formed in the rear-group lens frame 40.

A guide tube 61 functioning as a guide member, which is a holder, through which a rod 63 of an actuator 60 explained below, which presses and moves the moving lens unit 32 to a front side (an f direction shown in FIG. 3), is inserted is fixed to the holding rod 40a by screwing.

Note that, in the image pickup unit 30, a cover body 53 is firmly attached to outer surfaces of the projecting section 36b and the holding rod 40a by an adhesive or the like to cover an opening formed between the projecting section 36b of the holding frame 36 and the holding rod 40a of the rear-group lens frame 40.

That is, the image pickup unit 30 is formed in a closed structure in which the respective fixed frames fit with one another and the cover body 53 covers the opening formed by the holding frame 36 and the rear-group lens frame 40 to prevent dust and the like from entering the inside.

The guide tube 61 is formed in a substantially cylindrical body shape. A screw section 61a for screwing and fixing the guide tube 61 to the holding rod 40a is formed in an outer circumferential portion on a distal end side of the guide tube 61. An outward flange 61b is formed in a halfway portion of the guide tube 61. The outward flange 61b is screwed and fixed to the holding rod 40a from the rear until the outward flange 61b comes into contact with a proximal end face of the holding rod 40a.

A cover tube 65 of the actuator 60 explained below is extrapolated and fixed to a proximal end portion 61c behind the outward flange 61b of the guide tube 61.

In a distal end portion of the guide tube 61, an adjustment ring 62 that adjusts a position to the front and the back by a screwing amount with the screw section 61a to restrict a backward moving position of the moving lens frame 38 when a distal end comes into contact with a proximal end face of the protrusion section 38a of the moving lens frame 38.

After being adjusted to a predetermined position according to the screwing amount with the screw section 61a of the guide tube 61, the adjustment ring 62 is firmly fixed to the distal end portion of the guide tube 61 not to move by an adhesive or the like.

The solid-state-image-pickup-device-unit holding frame 41 holds a solid-state image pickup device unit 46. The solid-state image pickup device unit 46 includes, in order from a distal end, two optical members 42 and 43 such as cover glasses held by the solid-state-image-pickup-device-unit holding frame 41, a solid-state image pickup device chip 45 such as a CCD or a CMOS, on a front surface of which an image area 44 is located, and a laminated board 47.

Note that the solid-state image pickup device chip 45 and the laminated board 47 are electrically connected by a not-shown FPC or the like. The laminated board 47 is connected to a plurality of communication lines of a cable 50.

The cable 50 is inserted through and disposed on an inside of the endoscope 2. The cable 50 is electrically connected to the video processor 4 by the electric connector section 20 via the universal cord 17 and the scope cable 19.

A reinforcing frame 48 is fit to a proximal-end outer circumferential portion of the solid-state-image-pickup-device-unit holding frame 41. A coating member 49, which is a heat-shrinkable tube that covers up to a distal end portion of the cable 50, is provided in an outer circumference of the reinforcing frame 48.

Note that, in a space formed by the reinforcing frame 48 and the coating member 49 from a proximal end portion of the solid-state-image-pickup-device-unit holding frame 41, a protection agent such as an adhesive for keeping the solid-state image pickup device unit 46 watertight and protecting the solid-state image pickup device unit 46 is filled.

A configuration of the actuator 60 attached to the image pickup unit 30 is explained below.

The actuator 60 includes the rod 63 which is separable from the moving lens frame 38, the rod 63 being a contact member of a rigid bar body such as metal, a distal end of which is formed in a spherical shape, and a driving wire 64 connected to a proximal end side of the rod 63.

Note that a distal end of the driving wire 64 is inserted into a hole section formed in a proximal end portion of the rod 63. The driving wire 64 is thinly attached to the rod 63 by an adhesive or the like.

The actuator 60 includes the cover tube 65, which is a cover member made of metal connected to cover the proximal end portion 61c of the guide tube 61. The driving wire 64 is inserted through the cover tube 65.

In the actuator 60, as shown in FIG. 5 and FIG. 6, first, the rod 63, to which the driving wire 64 is connected, is inserted into the guide tube 61 from the proximal end portion 61c side of the guide tube 61. The cover tube 65 is connected to cover the proximal end portion 61c of the guide tube 61 and firmly attached by an adhesive or the like.

Note that, although not shown in the figure, the guide tube 61 shown in FIG. 5 and FIG. 6 is in a state in which the guide tube 61 is held by the holding rod 40a of the rear-group lens frame 40.

As shown in FIG. 7 and FIG. 8, the rod 63 inserted into the guide tube 61 has an outer diameter d2 smaller than a bore diameter d1 of the guide tube 61 over an entire length in an advancing and retracting direction. The rod 63 is insertable into and retractable from the guide tube 61. A linear guide for the rod 63 in the advancing and retracting direction is formed by the guide tube 61.

The driving wire 64 is inserted through and disposed on insides of the insertion section 9 and the operation section 10 in a state in which the driving wire 64 is covered with a sheath 66, a blade 67, and a heat-shrinkable tube 68. The driving wire 64 is pushed and pulled by operation of the operation lever 24 of the operation section 10 shown in FIG. 1.

Note that, as shown in FIG. 3 and FIG. 4, the tube-like sheath 66 covering the driving wire 64 is connected to extrapolate a proximal end portion of the cover tube 65. A ring member 65*a* for retaining the sheath 66 is provided in the proximal end portion of the cover tube 65.

The sheath 66 is coated on the heat-shrinkable tube 68, on an inner surface side of which the blade 67, which is a metal mesh tube, is provided. The blade 67 and the heat-shrinkable tube 68 are disposed to the front side of the sheath 66 to cover up to a halfway portion of the cover tube 65.

In the actuator 60 configured as explained above, the driving wire 64 advances and retracts according to the operation of the operation lever 24 provided in the operation section 10. Consequently, the rod 63 connected to the distal end of the driving wire 64 is driven such that a distal end portion of the rod 63 is led out forward from the guide tube 61 or the entire rod 63 is housed in the guide tube 61.

An operation for advancing and retracting the moving lens unit 32 with the actuator 60 of the image pickup unit 30 in the present embodiment is explained in detail below.

In the endoscope 2 in the present embodiment, as explained above, the actuator 60 of the image pickup unit 30 is driven by the operation of the operation lever 24 (see FIG. 1) of the operation section 10. The focusing function of focus adjustment or the zooming function for performing magnification adjustment such as wide/tele is performed on an object.

At this point, when the driving wire 64 is pushed and pulled on the basis of the operation of the operation lever 24 of the operation section 10, the rod 63 connected to the distal end of the driving wire 64 is driven to advance and retract while being linearly guided by the guide tube 61.

For example, when the operation lever 24 is operated as predetermined such that the moving lens unit 32 moves to the front side as shown in FIG. 3 from a state in which the moving lens unit 32 has been moved to the rear side (a state in which the driving wire 64 has been pulled backward) as shown in FIG. 4, the driving wire 64 is pushed to move to the front side. The distal end portion of the rod 63 housed in the guide tube 61 is led out forward from the guide tube 61.

At this point, a distal end of the rod 63 comes into contact with the proximal end face of the protrusion section 38*a* of the moving lens frame 38. The rod 63 pushes the protrusion section 38*a* to the front side (the f direction in FIG. 3), which is the first direction, resisting the urging force of the compression spring 52.

Consequently, the moving lens unit 32 moves forward (in an F direction in FIG. 3). Note that the forward movement of the moving lens unit 32 is restricted when the distal end face of the protrusion section 38*a* of the moving lens frame 38 comes into contact with the proximal end face of the projecting section 36*b* of the holding frame 36.

On the other hand, when the operation lever 24 is operated as predetermined such that the moving lens unit 32 moves to the rear side as shown in FIG. 4 from a state in which the moving lens unit 32 has been moved to the front side (a state in which the driving wire 64 has been pulled forward) as shown in FIG. 3, the driving wire 64 is pulled to move to the rear side. The distal end portion of the rod 63 led out forward from the guide tube 61 is housed in the guide tube 61.

At this point, the rod 63 moves backward while the distal end of the rod 63 comes into contact with the proximal end face of the protrusion section 38*a* of the moving lens frame 38. According to the movement, the moving lens unit 32 receives the urging force of the compression spring 52 and moves to the rear side (a B direction in FIG. 4), which is a second direction.

The backward movement of the moving lens unit 32 is restricted when the proximal end face of the protrusion section 38*a* of the moving lens frame 38 comes into contact with a distal end of the adjustment ring 62 provided in the distal end portion of the guide tube 61.

By operating the operation lever 24 and balancing the urging force of the compression spring 52 and a pressing force in the f direction of the rod 63 to the protrusion section 38*a*, it is also possible to prevent the protrusion section 38*a* from coming into contact with the proximal end face of the projecting section 36*b* and the distal end of the adjustment ring 62 and keep the protrusion section 38*a* in any position between the proximal end face of the projecting section 36*b* and the distal end of the adjustment ring 62.

As explained above, the image pickup unit 30 in the present embodiment disposed at the distal end portion 6 of the endoscope 2 is configured to be capable of advancing and retracting the moving lens unit 32 of the image pickup unit 30 according to predetermined operation of the operation lever 24 of the operation section 10 and performing the focusing function or the zooming function on the object.

Incidentally, in the image pickup unit 30 of the endoscope 2 explained above, when wear, deformation, or the like occurs in constituent members for advancing and retracting the moving lens unit 32 such as the rod 63 of the actuator 60 and the driving wire 64, only the actuator 60 can be easily replaced.

More specifically, when the actuator 60 is replaced, as shown in FIG. 9, a part of the cover tube 65 is cut and removed in a near position of the proximal end portion 61*c* of the guide tube 61.

When the driving wire 64 is pulled out backward from this state, as shown in FIG. 10, the rod 63 in the guide tube 61 is removed.

Finally, a part of the cover tube 65 remaining in the proximal end portion 61*c* of the guide tube 61 is peeled. In this way, the actuator 60, in which wear, deformation, or the like occurs in the constituent members, is easily detached from the image pickup unit 30.

When a new actuator 60 is assembled to the image pickup unit 30, as explained above, the rod 63, to which the driving wire 64 is connected, is inserted into the guide tube 61. The cover tube 65 is connected to cover the proximal end portion 61*c* of the guide tube 61 and firmly attached by an adhesive or the like (see FIG. 5 and FIG. 6).

Note that, although not shown in the figure, the guide tube 61 shown in FIG. 9 and FIG. 10 is in a state in which the guide tube 61 is held by the holding rod 40*a* of the rear-group lens frame 40.

In this way, in the image pickup unit 30, in order to make it possible to easily replace only the actuator 60, the rod 63 inserted into the guide tube 61 is not fixed to the moving lens unit 32. The rod 63 has the outer diameter d2 smaller than the bore diameter d1 of the guide tube 61 over the entire length in the advancing and retracting direction. If the cover tube 65 is cut, the rod 63 can be easily removed from the guide tube 61.

Note that, in the image pickup unit 30, when the actuator 60 is replaced, in a state in which the cover tube 65 is cut and the rod 63 is removed, only a hole portion of the guide tube 61, in which the rod 63 of the actuator 60 is housed, communicates with the inside and opens.

In this state, in the image pickup unit 30, dust and the like less easily enter the inside from the hole portion of the guide tube 61, the dust and the like do not adhere to the objective lens to adversely affect an image. Slidability of the moving lens frame is not deteriorated, either.

Therefore, in the image pickup unit 30, even when wear, deformation, or the like occurs in the constituent members configuring the actuator 60, only the actuator 60 can be replaced. Therefore, it is unnecessary to replace the entire image pickup unit 30 including the solid-state image pickup device unit 46 including the solid-state image pickup device chip 45, which is an expensive image sensor.

According to the above explanation, the image pickup unit 30 in the present embodiment can be configured such that, when the members such as the rod 63 that advances and retracts the moving lens unit 32 and the driving wire 64 are, for example, worn or deformed, only the members can be easily replaced and the entire image pickup unit 30 including the entire expensive image sensor does not need to be replaced.

Note that, a configuration may be adopted in which, in the image pickup unit 30, the driving wire 64 for advancing and retracting the moving lens unit 32 is configured using a shape memory alloy wire formed from a shape memory alloy that contracts when heated and expands when cooled.

First Modification

As shown in FIG. 11 to FIG. 13, in the actuator 60, a plurality of, in this modification, three slits 65b may be provided as the distal end portion of the cover tube 65 extrapolated and firmly attached to the proximal end portion 61c of the guide tube 61.

Since the plurality of slits 65b are provided, the cover tube 65 can be easily peeled off from the proximal end portion 61c of the guide tube 61 during replacement of the actuator 60.

Second Modification

Further, as shown in FIG. 14 to FIG. 16, in the actuator 60, a configuration may be adopted in which a male screw is formed at the proximal end portion 61c of the guide tube 61 and, in this modification, a hexagon nut section 69, in which a female screw detachably screwing with the male screw is formed, is provided at the distal end of the cover tube 65.

The cover tube 65 can be easily attached and detached by tightening or loosening the nut section 69 with respect to the proximal end portion 61c of the guide tube 61 during attachment or during replacement of the actuator 60.

Reference Example

A reference example in the image pickup unit 30 of the present invention is explained below.

Figure 17:
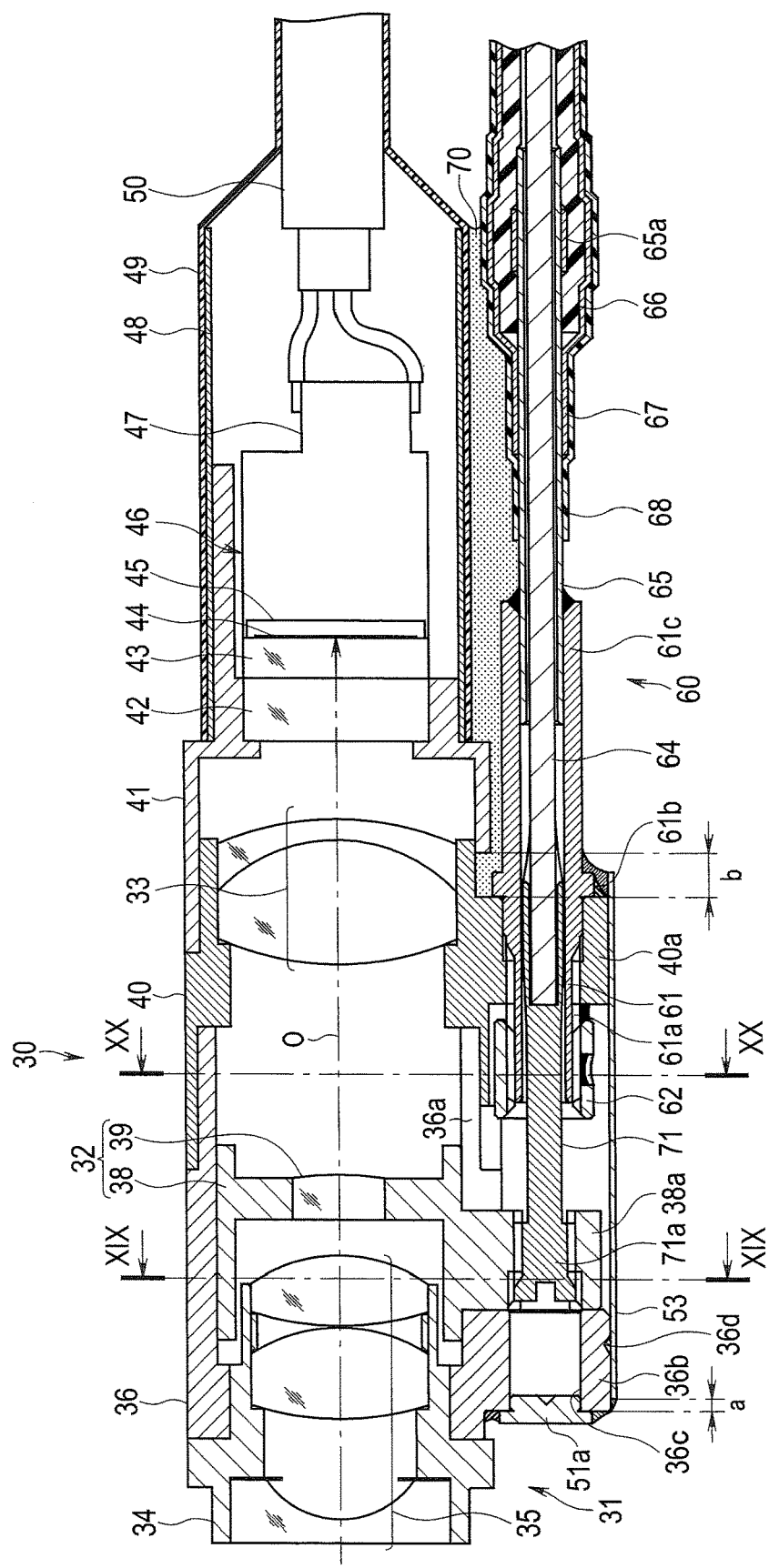
FIG. 17 is a sectional view showing a configuration of an image pickup unit of a reference example.
Figure 18:
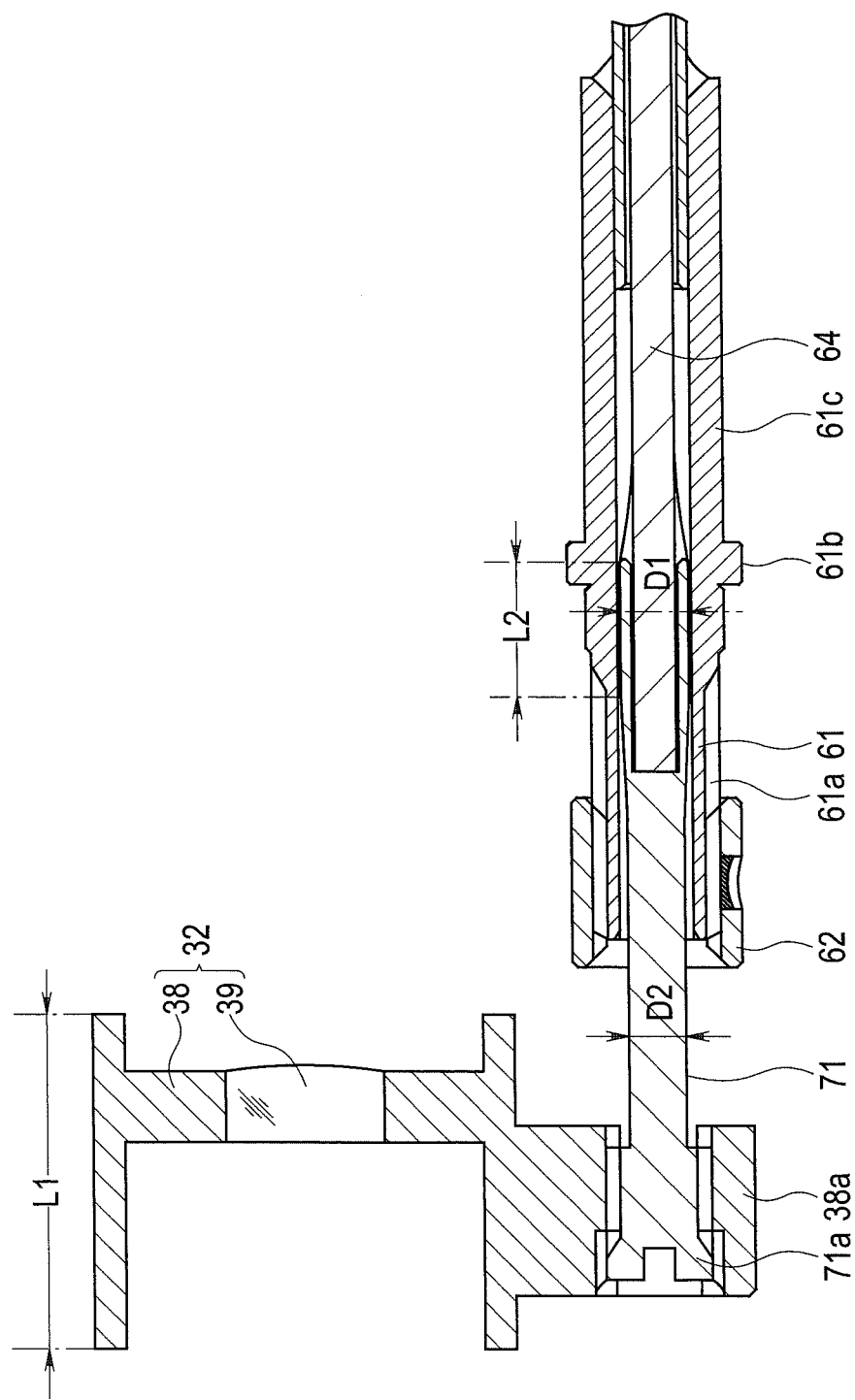
FIG. 18 is a sectional view showing a configuration of a moving lens unit and an actuator of the reference example.
Figure 19:
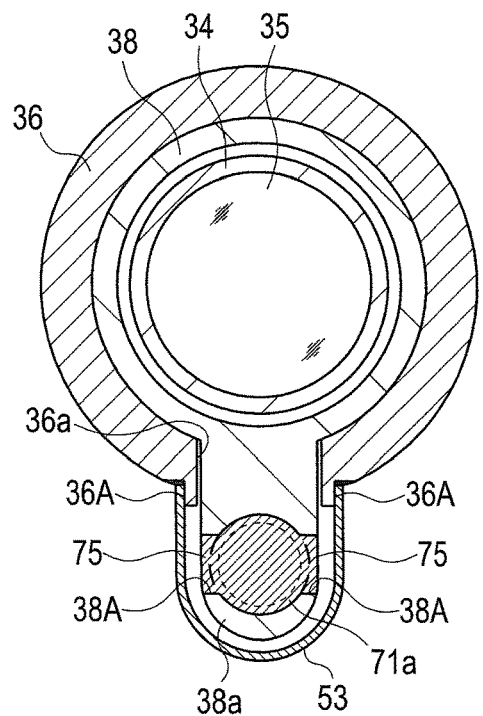
FIG. 19 is a sectional view taken along line XIX-XIX in FIG. 17.
Figure 20:
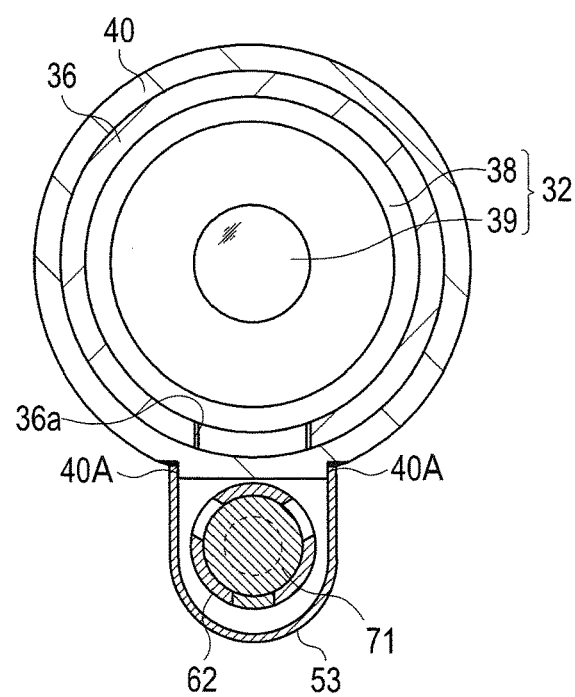
FIG. 20 is a sectional view taken along line XX-XX in FIG. 17.

FIG. 17 is a sectional view showing a configuration of the image pickup unit of the reference example. FIG. 18 is a sectional view showing a configuration of a moving lens unit and an actuator of the reference example. FIG. 19 is a sectional view taken along line XIX-XIX in FIG. 17. FIG. 20 is a sectional view taken along line XX-XX in FIG. 17.

Note that, in the following explanation, components same as the components of the image pickup unit 30 explained above are denoted by the same reference numerals and signs. Detailed explanation of the components is omitted.

As shown in FIG. 17, the image pickup unit 30 in this reference example disposed in the endoscope 2 includes a bar-like coupling shaft 71 instead of the rod 63 of the actuator 60 unlike the configuration including the rod 63.

A connecting section 71a connected to the moving lens unit 32 is provided at a distal end of the coupling shaft 71. More specifically, the actuator 60 is fixed when a connecting section 71a of the coupling shaft 71 screws in the protrusion section 38a provided in the moving lens frame 38 of the moving lens unit 32.

In the endoscope 2 in this reference example, as explained above, the actuator 60 of the image pickup unit 30 is driven by the operation of the operation lever 24 (see FIG. 1) of the operation section 10 and the focusing function of focus adjustment or the zooming function for performing magnification adjustment such as wide/tele is performed on the object.

In the driving of the actuator 60 at this point, in the same manner as explained above, when the driving wire 64 is pushed and pulled on the basis of the operation of the operation lever 24 of the operation section 10, the coupling shaft 71 connected to the distal end of the driving wire 64 is driven to advance and retract while being linearly guided by the guide tube 61.

Since the coupling shaft 71 is connected to the moving lens unit 32, the moving lens unit 32 is driven to advance and retract according to the advance and the retraction of the coupling shaft 71.

In this reference example, as in the embodiment, the forward movement of the moving lens unit 32 is restricted when the distal end face of the protrusion section 38a of the moving lens frame 38 comes into contact with the proximal end face of the projecting section 36b of the holding frame 36. The backward movement of the moving lens unit 32 is restricted when the proximal end face of the protrusion section 38a of the moving lens frame 38 comes into contact with the distal end of the adjustment ring 62 provided at the distal end portion of the guide tube 61.

Incidentally, the coupling shaft 71 is smaller in diameter on the connecting section 71a side, which a distal end side, than a proximal end portion. More specifically, as shown in FIG. 18, the coupling shaft 71 is gradually reduced in diameter to the distal end side with respect to a diameter D1 of the proximal end portion. A diameter D2 smaller than the diameter D1 of the proximal end portion (D1>D2) is set from a halfway portion to a distal end.

That is, the proximal end side of the coupling shaft 71 is formed thick with the diameter D1 at a predetermined length. The distal end side of the coupling shaft 71 is formed thin with the diameter D2 at a predetermined length. Consequently, during the advance and the retraction, a small diameter portion of the coupling shaft 71 does not come into contact with a distal end opening portion of the guide tube 61.

With such a configuration, in the image pickup unit 30, even if fluctuation, a tilt, and the like caused by assembly tolerances of various components and a posture change due to bending operation of the bending section 7 occur, the small diameter portion of the coupling shaft 71 does not interfere with the guide tube 61. It is possible to reduce sliding resistance during the advance and the retraction.

Further, as shown in FIG. 18, the moving lens frame 38 of the moving lens unit 32 has length L1 in the advancing and retracting direction (a direction along the photographing optical axis O in FIG. 17). In the moving lens unit 32, by setting the length L1 of the moving lens frame 38 as large as possible, it is possible to suppress a tilt at a time when the moving lens unit 32 advances and retracts in the holding frame 36.

The coupling shaft 71 is connected and fixed to the moving lens unit 32, the tilt of which is suppressed. Therefore, a tilt of the coupling shaft 71 is also suppressed. Length L2 of the large diameter portion of the proximal end portion slid and linearly guided by the guide tube 61 during the advance and the retraction is reduced to reduce sliding resistance. Note that the large diameter portion of the coupling shaft 71 has the length L2 smaller than the length L1 of the moving lens frame 38 (L1>L2).

Other various contrivances in the image pickup unit 30 are explained below.

First, as shown in FIG. 17, a lid body 51a is bonded to an opening section in the front of the through-hole 36c formed in the projecting section 36b of the holding frame 36. The through-hole 36c of the projecting section 36b is formed to have a certain degree of length (depth) such that an unnecessary adhesive applied during the bonding of the lid body 51a flows into the through-hole 36c.

Consequently, a contrivance is made to prevent the unnecessary adhesive from protruding to a surface side of the projecting section 36b when the lid body 51a is bonded to the through-hole 36c of the projecting section 36b.

The cover body 53 that bridges and covers the projecting section 36b of the holding frame 36 and the holding rod 40a of the rear-group lens frame 40 is bonded and fixed to the projecting section 36b and the holding rod 40a by an adhesive. In the projecting section 36b, a peripheral groove 36d, into which the unnecessary adhesive flows, is formed in a portion covered by the cover body 53 such that the adhesive does not protrude from the cover body 53.

Further, the cover body 53 is firmly attached to a position shifted backward by a predetermined distance "a" from a distal end face of the projecting section 36b such that the unnecessary adhesive can be easily wiped off even if the unnecessary adhesive protrudes at a distal end of the cover body 53. In this way, a contrivance is made to improve workability during the firm attachment of the projecting section 36b of the holding frame 36/the holding rod 40a of the rear-group lens frame 40 and the cover body 53.

The holding frame 36 and the rear-group lens frame 40 are fit with each other and firmly attached by an adhesive. At this point, the unnecessary adhesive protruding from the distal end side of the rear-group lens frame 40 is wiped off. Thereafter, an adhesive for completely sealing a joining portion is applied in a circumferential direction of a distal end of the rear-group lens frame 40.

Therefore, in the holding frame 36, a groove section 36e for an indicator for specifying a range in which the adhesive is applied near the distal end of the fit rear-group lens frame 40 is formed in the circumferential direction. A contrivance is made to improve workability during the firm attachment to the rear-group lens frame 40.

The rear-group lens frame 40 and the solid-state-image-pickup-device-unit holding frame 41 are also fit with each other and firmly attached by an adhesive. At this point, in order to allow an unnecessary adhesive to escape on a distal end side of the solid-state-image-pickup-device-unit holding frame 41, a groove section 40b is formed in the circumferential direction on the rear-group lens frame 40 side and a step-like adhesive reservoir 40c for accumulating the unnecessary adhesive on the front side of the groove section 40b is formed.

Consequently, a contrivance is made to prevent the unnecessary adhesive from protruding to the surface side during the firm attachment of the rear-group lens frame 40 and the solid-state-image-pickup-device-unit holding frame 41.

Note that the solid-state-image-pickup-device-unit holding frame 41 is formed in a shape for separating from the holding rod 40a of the rear-group lens frame 40 by a predetermined distance "b" in a state in which the solid-state-image-pickup-device-unit holding frame 41 is fit in the rear-group lens frame 40. Consequently, a contrivance is made to prevent interference with the guide tube 61 provided in the holding rod 40a.

In the image pickup unit 30, a gap between the actuator 60 and the solid-state-image-pickup-device-unit holding frame 41 side is filled with a hard adhesive 70. Consequently, a contrivance is made to prevent, for example, a blast during the driving of the actuator 60.

Further, in the holding frame 36 and the rear-group lens frame 40, as shown in FIG. 19 and FIG. 20, in a state in which the projecting section 36b and the holding rod 40a are fit with each other, plane sections 36A and 40A continuous in the same plane are formed between the projecting section 36b and the holding rod 40a when respective end faces of the projecting section 36b and the holding rod 40a collide with each other.

An edge side portion of the cover body 53 is bonded to the plane sections 36A and 40A. Consequently, a contrivance is made to completely seal the projecting section 36b and the holding rod 40a.

Note that, as shown in FIG. 19, in the protrusion section 38a of the moving lens frame 38, two hole sections 38A for filling an adhesive 75 and firmly attaching the connecting section 71a of the coupling shaft 71 are formed from a side direction.

Consequently, a contrivance is made to firmly fix the coupling shaft 71 to the protrusion section 38a of the moving lens frame 38.

The inventions described in the respective embodiments explained above are not limited to the embodiments and the modifications.

Besides, at an implementation stage, it is possible to implement various modifications in a range not departing from the gist of the inventions. Further, inventions at various stages are included in the embodiments. Various inventions can be extracted according to appropriate combinations in a disclosed plurality of constituent elements.

For example, when the problems to be solved by the invention can be solved and the effects described in the effect of the invention can be obtained even if several constituent elements are deleted from all the constituent elements described in the embodiments, a configuration from which the constituent elements are deleted can be extracted as an invention.

What is claimed is:

1. An image pickup unit comprising:
   a fixed frame configured to hold an objective lens;
   a moving frame disposed in the fixed frame to be movable in a first direction along a photographing optical axis and a second direction opposite to the first direction, and provided with a moving lens;
   an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and
   a tubular guide member fixed to the fixed frame and including a guide hole through which the contact member is inserted to be guided to advance and retract, wherein a cover member disposed on the actuator, a distal end portion of the cover member being connected to a proximal end portion of the guide member, and the cover member covering the driving wire, wherein the contact member has an outer diameter smaller than an inner diameter of the guide hole and is insertable into and retractable from the guide member, the cover member includes a peeling section in which a plurality of slits are formed in a position where the cover member is firmly attached to the proximal end portion of the guide member so as to cover the proximal end portion, the peeling section being cuttable when the actuator is replaced, and the driving wire includes an exposed section exposed in a state in which the cover member is peeled in the peeling section, the driving wire being configured to be pulled out from the guide member toward a proximal end side of the guide member, the exposed section enabling the contact member fixed to the driving wire to be removed from the proximal end side of the guide member.

2. An endoscope comprising the image pickup unit according to claim 1, wherein the image pickup unit is disposed at a distal end portion of an insertion section.

3. An endoscope comprising the image pickup unit according to claim 1, further comprising a spring disposed in the fixed frame and configured to urge the moving frame in the second direction.

4. An image pickup unit comprising:

a fixed frame configured to hold an objective lens;

a moving frame disposed in the fixed frame to be movable in a first direction along a photographing optical axis and a second direction opposite to the first direction, and provided with a moving lens;

an actuator including a bar-like contact member fixed to a distal end of a driving wire to be separable from the moving frame and advanced and retracted by pushing and pulling of the driving wire, the actuator moving the moving frame in the first direction when the contact member moves in the first direction and comes into contact with and presses the moving frame; and a tubular guide member fixed to the fixed frame and including a guide hole through which the contact member is inserted to be guided to advance and retract, wherein a cover member disposed on the actuator, a distal end portion of the cover member being connected to a proximal end portion of the guide member, and the cover member covering the driving wire, wherein the contact member has an outer diameter smaller than an inner diameter of the guide hole and is insertable into and retractable from the guide member, the cover member includes a cuttable section formed to be capable of being cut when the actuator is replaced, in a position where only the driving wire is covered near the proximal end portion of the guide member, and the driving wire includes an exposed section exposed in a state in which the cover member is cut in the cuttable section, the driving wire being configured to be pulled out from the guide member toward a proximal end side of the guide member, the exposed section enabling the contact member fixed to the driving wire to be removed from the proximal end side of the guide member.

5. An endoscope comprising the image pickup unit according to claim 4, wherein the image pickup unit is disposed at a distal end portion of an insertion section.

6. An endoscope comprising the image pickup unit according to claim 4, further comprising a spring disposed in the fixed frame and configured to urge the moving frame in the second direction.

\* \* \* \* \*